US008671472B2

(12) United States Patent
Groner et al.

(10) Patent No.: US 8,671,472 B2
(45) Date of Patent: Mar. 18, 2014

(54) AIR CONTROL AND AROMATHERAPY MODULE

(76) Inventors: David M. Groner, Oil City, PA (US); Devin J. Callihan, Leeper, PA (US); Brian A. Milford, Venus, PA (US)

( * ) Notice: Subject to any disclaimer, the term of this patent is extended or adjusted under 35 U.S.C. 154(b) by 670 days.

(21) Appl. No.: 12/469,275

(22) Filed: May 20, 2009

(65) Prior Publication Data

US 2010/0294849 A1 Nov. 25, 2010

(51) Int. Cl.

| | |
|---|---|
| ***A61H 33/02*** | (2006.01) |
| ***A61H 33/00*** | (2006.01) |
| ***A47K 3/02*** | (2006.01) |
| ***A47K 3/00*** | (2006.01) |
| ***E04H 4/14*** | (2006.01) |
| ***A61L 9/04*** | (2006.01) |
| ***A61L 9/12*** | (2006.01) |

(52) U.S. Cl.

USPC .......... 4/559; 4/492; 4/541.1; 4/541.4; 239/9; 239/58; 239/428.5

(58) Field of Classification Search

USPC ............. 239/302, 310, 313, 315, 325, 54, 58, 239/55, 57, 60, 6, 8, 9, 428.5; 422/306; 128/66; 4/492, 496, 541.1, 541.4, 4/541.6, 559; 607/81, 85; 601/157

See application file for complete search history.

(56) References Cited

U.S. PATENT DOCUMENTS

| | | | | |
|---|---|---|---|---|
| 3,366,110 A * | 1/1968 | Gaylord, Jr. | .................. | 604/290 |
| 3,571,820 A | 3/1971 | Jacuzzi | | |
| 3,745,994 A | 7/1973 | Kane | | |
| 3,886,936 A * | 6/1975 | Wehrenberg | .................. | 601/157 |
| 3,986,217 A | 10/1976 | Doerr et al. | | |
| 3,986,340 A * | 10/1976 | Bivins, Jr. | ...................... | 62/50.2 |
| 4,057,372 A | 11/1977 | Johnson et al. | | |
| 4,325,149 A | 4/1982 | Moreland | | |
| 4,340,039 A | 7/1982 | Hibbard et al. | | |
| 4,592,100 A * | 6/1986 | Robertson et al. | ............. | 4/541.4 |
| 4,637,080 A | 1/1987 | Hutchinson | | |
| 4,785,484 A | 11/1988 | Sargent | | |
| 4,823,413 A | 4/1989 | Chalberg et al. | | |
| 4,901,379 A | 2/1990 | Chalberg et al. | | |
| 4,918,768 A | 4/1990 | DeSousa et al. | | |
| 5,794,280 A * | 8/1998 | Hansen et al. | ................. | 4/541.1 |
| 5,799,345 A * | 9/1998 | Hansen et al. | .................... | 4/584 |
| 5,983,416 A * | 11/1999 | Idland | ............................ | 4/541.1 |
| 6,405,387 B1 * | 6/2002 | Barnes | ........................... | 4/541.2 |
| 6,581,217 B2 | 6/2003 | Marcos | | |
| 6,681,414 B1 | 1/2004 | May et al. | | |
| 6,723,233 B1 | 4/2004 | Barnes | | |
| 6,859,953 B1 | 3/2005 | Christensen | | |
| 6,968,581 B2 | 11/2005 | Christensen | | |
| 7,060,180 B1 | 6/2006 | Barnes | | |
| 2002/0148911 A1 * | 10/2002 | Beck et al. | .................... | 239/310 |
| 2008/0168992 A1 * | 7/2008 | Spector | .................... | 128/207.18 |
| 2009/0158519 A1 * | 6/2009 | Castellote et al. | ................ | 4/559 |

* cited by examiner

*Primary Examiner* — Darren W Gorman

(74) *Attorney, Agent, or Firm* — The Webb Law Firm

(57) ABSTRACT

An air control and aromatherapy module for a jetted tub comprising an air control member having a body portion defining an intake opening, a scent container defining a scent opening, and a housing having a body portion. The scent container is positioned within the body portion of the air control member. The air control member and the scent container are at least partially disposed within the body portion of the housing. The air control member and the housing define a central passageway and the scent opening of the scent container is in fluid communication with the central passageway. A method of providing aromatherapy to a jetted tub is also disclosed.

11 Claims, 7 Drawing Sheets

AIR CONTROL AND AROMATHERAPY MODULE

BACKGROUND OF THE INVENTION

1. Field of the Invention

The present invention relates to whirlpool bathtubs, spas, hot tubs and, more specifically, to air control modules and aromatherapy modules for whirlpool bathtubs, spas and hot tubs.

2. Description of Related Art

Whirlpool bathtubs, spas, and hot tubs typically circulate water between a water intake and jets positioned beneath the water line of the whirlpool tub, spa or bath. Further, air is mixed with the water to increase the force on the body or skin of the user. Certain tub or spa designs have incorporated a unit to introduce a scent or aromatherapy into the bathing well when the air is mixed with the water before exiting the jets.

Referring to FIG. 1, a prior art system 1 for incorporating aromatherapy into air exiting the jets of a whirlpool tub is disclosed. The prior art system 1 includes an air control unit 3 secured to the bathtub deck 5 and an aromatherapy unit 7 spaced from the air control unit 3 and secured to the bathtub deck 5. The air control unit 3 is connected to the aromatherapy unit 7 via a 90 degree L-fitting 9 and piping 11. The aromatherapy unit 7 includes a canister (not shown) containing an aromatherapy catalyst (beads, crystals, liquid, etc.) positioned within the aromatherapy unit 7 such that air introduced from the air control unit 3 passes through the L-fitting 9 and piping 11 through the canister to an outlet 15. The outlet 15 leads to jets (not shown) thereby introducing the scent or aromatherapy into the bathing well.

Various other designs for introducing aromatherapy in a tub or spa are known. In particular, U.S. Pat. Nos. 7,060,180; 6,723,233; and 6,405,387 to Barnes are generally directed to a jetted apparatus for tubs and spas. The apparatus comprises a structure for providing aromatherapy which may be combined with an ozone generator. The disclosed aromatherapy structure includes an enclosure in which an adapter is provided having a female threaded region extending into an interior of the enclosure and including a port adapted to receive a tube connecting the enclosure to an ozone generator. A cylindrical housing is open at both ends and has a male threaded region at one of its ends which is screwed into a female threaded region of an adapter. Ozone generated by the ozone generator flows through a disc shaped diffuser, which includes a porous material and serves to receive an aromatherapy compound or scented liquid in order to enrich ozone passing through the housing and the diffuser with an aromatherapy compound or scent vapor. Further, the enclosure includes a port which is connected with a tube to an air tube downstream of an air control valve to allow a fluid communication between the air tube and the enclosure.

U.S. Pat. No. 6,581,217 to Marcos is directed to a jetted bathtub in which a scent package is placed in a pipe section of the piping of the bathtub. As air flows through the pipe section, it passes through the scent package and picks up scent vapor from the scent package. Subsequently, the air scent mixture is blown out of an air outlet and directed to an area above the bathtub.

SUMMARY OF THE INVENTION

In one embodiment, an air control and aromatherapy module for a jetted tub is disclosed. The air control and aromatherapy module comprises an air control member having a body portion defining an intake opening, and a scent container defining a scent opening. The scent container is positioned adjacent to the air control member. The air control member defines a central passageway, and the scent opening of the scent container is in fluid communication with the central passageway. The air control and aromatherapy module may further comprise a housing having a body portion that at least partially encloses the air control member and the scent container with the housing further defining the central passageway. The scent container may comprise a body portion and an end portion defining a receiving space for an aromatherapy catalyst. The scent container may be positioned within the body portion of the air control member with the end portion of the scent container defining the scent opening. The air control member may further comprise a closed top positioned on an end of the body portion of the air control member.

Further, the body portion of the air control member may be cylindrical in shape having an inner threaded surface and an outer threaded surface, the body portion of the housing may be cylindrical in shape having an inner threaded surface, and the scent container may be cylindrical in shape having an outer threaded surface. The outer threaded surface of the scent container engages the inner threaded surface of the air control member, and the outer threaded surface of the air control member engages the inner threaded surface of the housing. The body portion of the housing may comprise an outer threaded portion with a housing nut engaged with the outer threaded portion of the housing. The housing may further comprise a flange extending from the body portion of the housing with the flange of the housing and the housing nut being configured to engage a tub deck.

In a further embodiment, an air control and aromatherapy module for a jetted tub comprising an air control member having a body portion defining an intake opening, a scent container defining a scent opening, and a housing having a body portion. The scent container is positioned within the body portion of the air control member. The air control member and the scent container are at least partially disposed within the body portion of the housing. The air control member and the housing define a central passageway and the scent opening of the scent container is in fluid communication with the central passageway.

In another embodiment, a method of providing aromatherapy to a jetted tub is disclosed. The method of providing aromatherapy to a jetted tub comprises the step of directing air through an intake opening of an air control member such that air enters the intake opening of the control member and passes through a scent container positioned within the air control member. The air control member and the scent container may be at least partially disposed within a housing. The method may further comprise the step of displacing the air control member relative to the housing to control a volume of the air directed through the intake opening of the air control member.

DESCRIPTION OF THE PREFERRED EMBODIMENTS

For purposes of the description hereinafter, spatial orientation terms, if used, shall relate to the referenced embodiment as it is oriented in the accompanying drawing figures or otherwise described in the following detailed description. However, it is to be understood that the embodiments described hereinafter may assume many alternative variations and embodiments. It is also to be understood that the specific devices illustrated in the accompanying drawing figures and described herein are simply exemplary and should not be considered as limiting.

Figure 1:
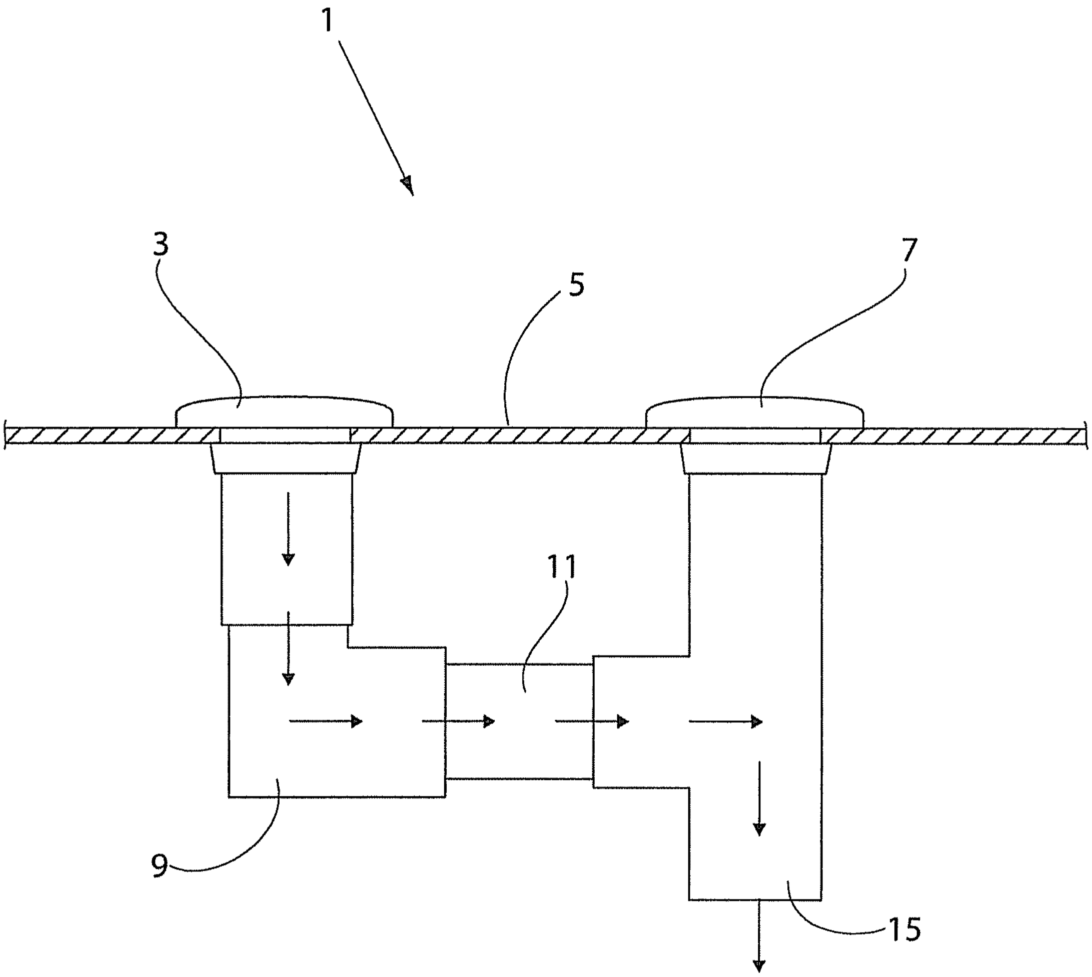
(Prior Art) FIG. 1
FIG. 1 is a side view of a prior art system for incorporating aromatherapy into air exiting jets of a tub.
Figure 2:
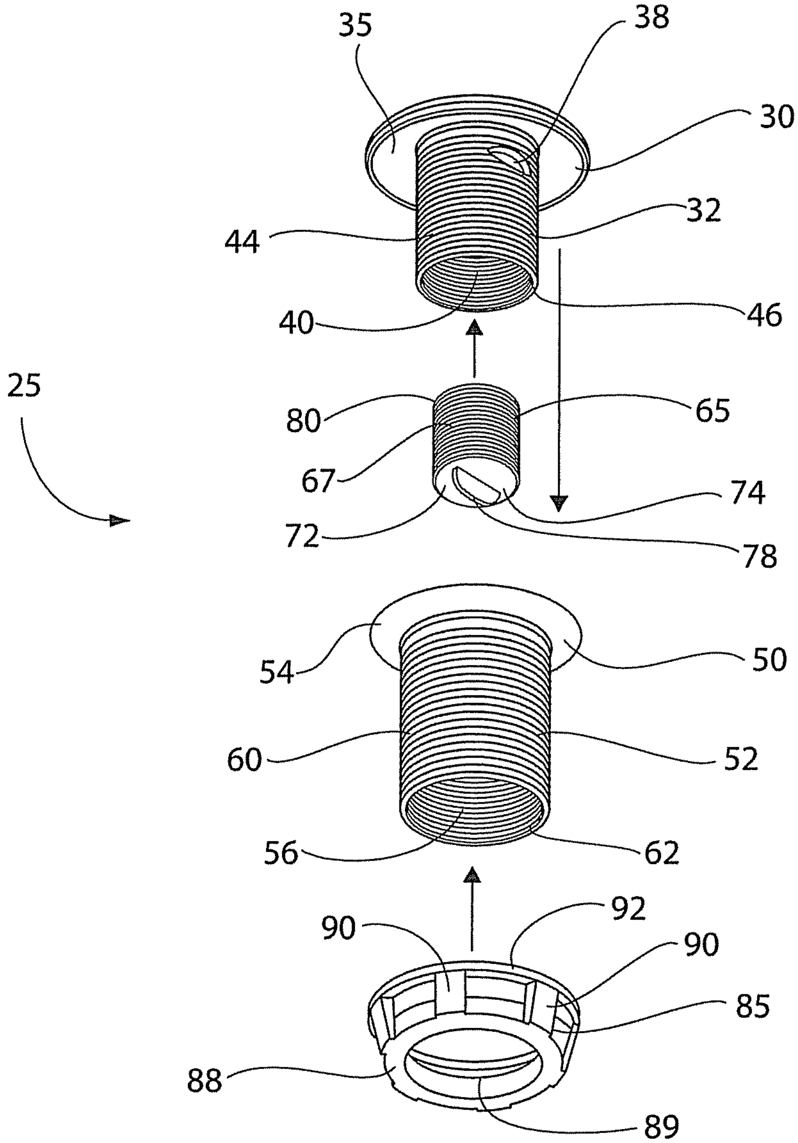
FIG. 2 is an exploded perspective view of an air control and aromatherapy module according to one embodiment of the present invention.
Figure 3:
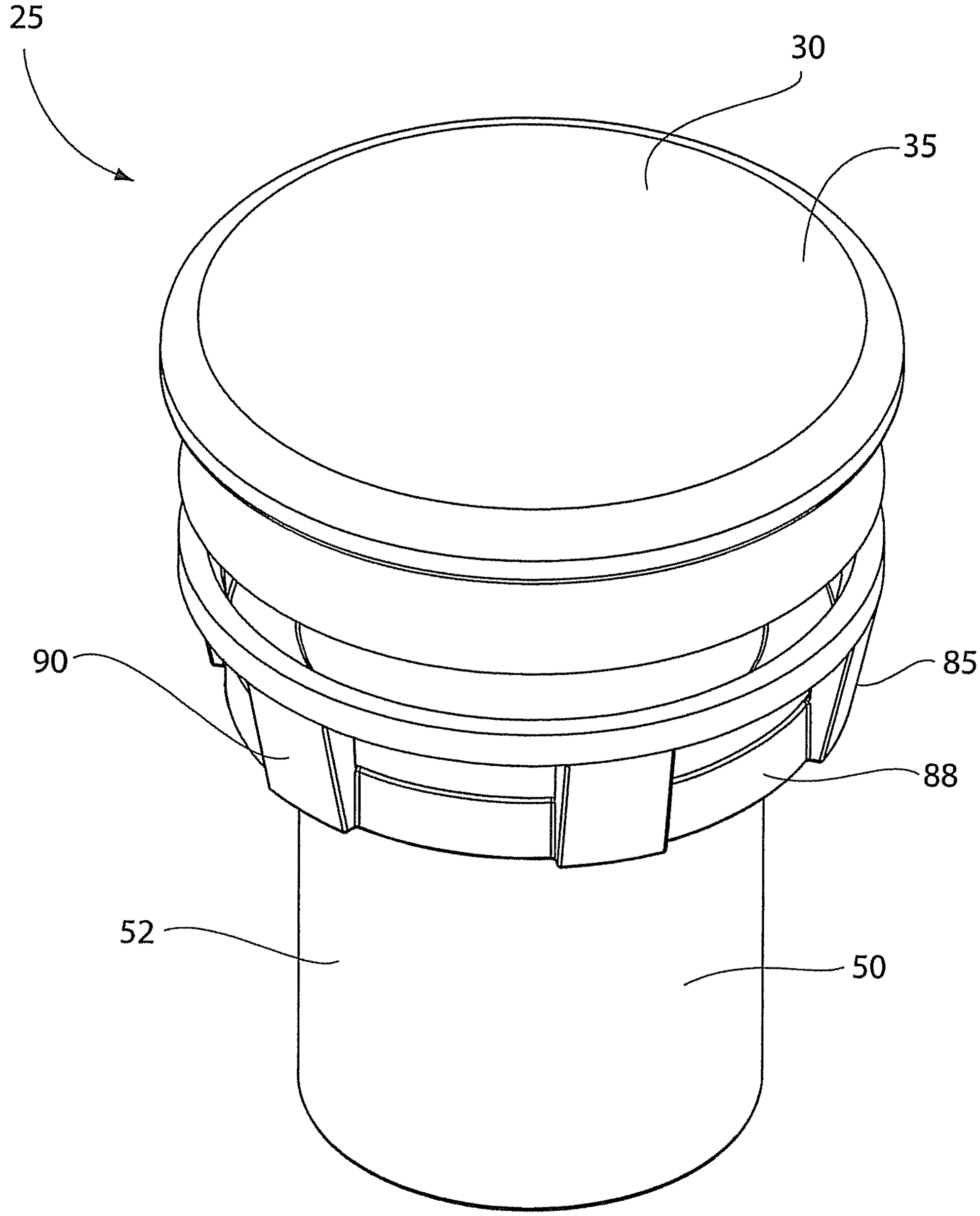
FIG. 3 is a perspective view of the module shown in FIG. 2.
Figure 4:
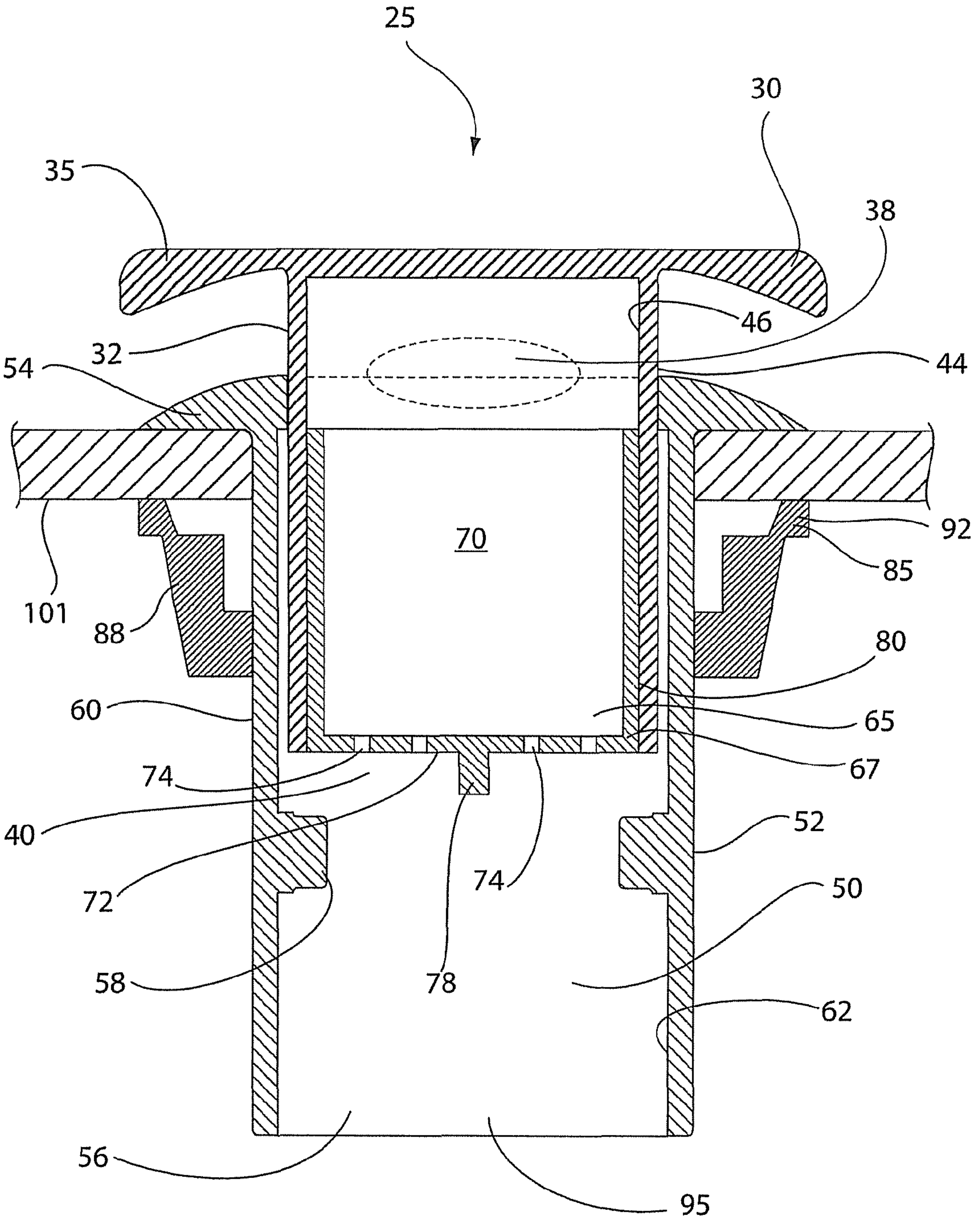
FIG. 4 is a cross-sectional view of the module shown in FIG. 2.

Referring to FIGS. 2-4, an air control and aromatherapy module 25 according to one embodiment is disclosed. The air control and aromatherapy module 25 includes an air control member 30, a housing 50, a scent container 65, and a housing nut 85.

Figure 5:
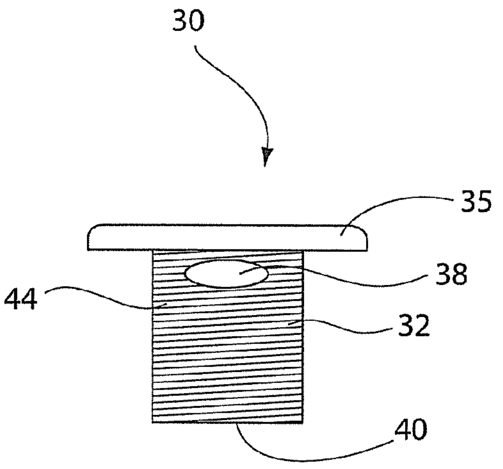
FIG. 5 is a side view of an air control member according to one embodiment of the present invention.
Figure 6:
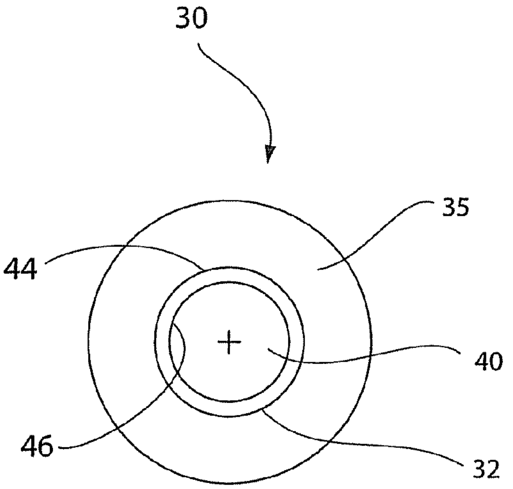
FIG. 6 is a bottom view of the air control member shown in FIG. 5.

Referring to FIGS. 5 and 6, the air control member 30 includes a body portion 32 having a cylindrical shape and a closed top 35 positioned on an end of the body portion 32. The body portion 32 of the air control member 30 defines an intake opening 38 extending radially through the body portion 32. The body portion 32 of the air control member 30 further defines a central opening 40 extending longitudinally through the body portion 32. The intake opening 38 has an elliptical shape, although other shapes and configurations for the intake opening 38 may be used. The body portion 32 of the air control member 30 also includes an outer threaded surface 44 and an inner threaded surface 46.

Figure 7:
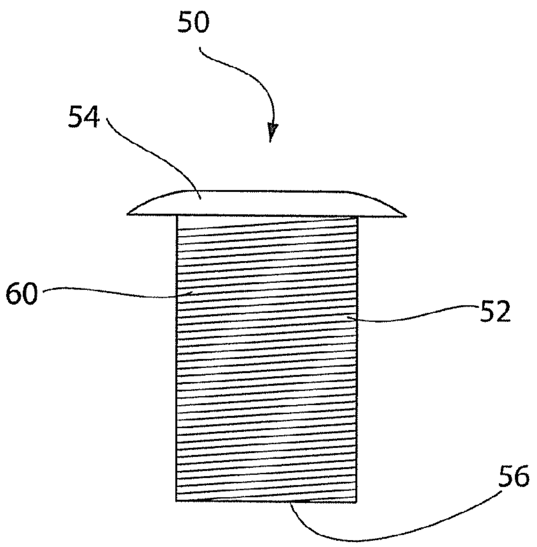
FIG. 7 is a side view of a housing according to one embodiment of the present invention.
Figure 8:
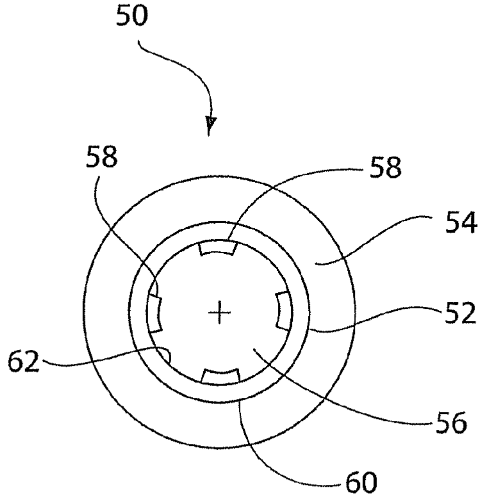
FIG. 8 is a bottom view of the housing shown in FIG. 7.

Referring to FIGS. 7 and 8, the housing 50 includes a body portion 52 having a cylindrical shape and a flange 54 extending outwardly from the body portion 52. The body portion 52 of the housing 50 defines a central opening 56 extending longitudinally through the body portion 52. Further, a plurality of tab members 58 extend radially inward from the body portion 52 of the housing 50 and are positioned intermediately between the ends of the body portion 52. The body portion 52 of the housing 50 also includes an outer threaded surface 60 and an inner threaded surface 62.

Figure 9:
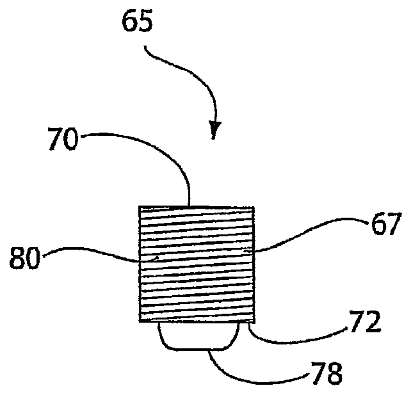
FIG. 9 is a side view of a scent container according to one embodiment of the present invention.
Figure 10:
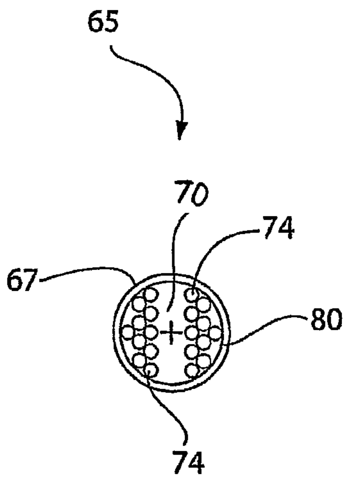
FIG. 10 is top view of the scent container shown in FIG. 9.

Referring to FIGS. 9 and 10, the scent container 65 includes a body portion 67 having a cylindrical shape. The body portion 67 of the scent container 65 defines a receiving space 70 for an aromatherapy catalyst (not shown), such as beads or crystals. The body portion 67 of the scent container 65 also includes an end portion 72 that defines a plurality of scent openings 74. Although a plurality of scent openings 74 are shown in FIG. 10, the scent container 65 may include one or more scent openings 74. The end portion 72 also includes a protrusion 78 extending outwardly from the end portion 72. Further, the body portion 67 of the scent container 65 includes an outer threaded surface 80.

Figure 11:
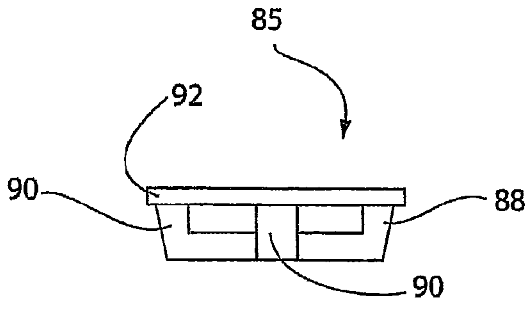
FIG. 11 is a side view of a housing nut according to one embodiment of the present invention.
Figure 12:
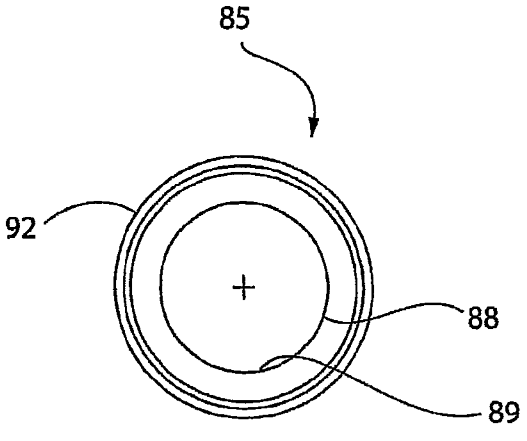
FIG. 12 is a bottom view of the housing nut shown in FIG. 11.

Referring to FIGS. 11 and 12, the housing nut 85 has an annular body 88 having a threaded inner surface 89. The annular body 88 includes a plurality of longitudinal ribs 90 extending radially outward from the annular body 88 and a flange 92 extending radially outward from the annular body 88.

Referring again to FIGS. 2-4, the air control and aromatherapy module 25 is assembled by positioning the scent container 65 within the central opening 40 of the body portion 32 of the air control member 30. In particular, the scent container 65 is threaded within the body portion 32 of the air control member 30 through engagement of the outer threaded surface 80 of the scent container 65 with the inner threaded surface 46 of the air control member 30. A user may grasp the protrusion 78 extending from the end portion 72 of the scent container 65 to assist in threading the scent container 65 within the air control member 30. Accordingly, the scent container 65 may be selectively inserted and removed from the air control module 30. The body portion 32 of the air control member 30 with the scent container 65 positioned therein is then positioned within the central opening 56 of the body portion 52 of the housing 50. More specifically, the air control member 30 is threaded within the body portion 52 of the housing 50 through engagement of the outer threaded surface 44 of the air control member 30 with the inner threaded surface 62 of the housing 50. When the air control and aromatherapy module 25 is fully assembled, the air control member 30 and the housing 50 define a central passageway 95 formed by the central openings 40, 56 of the air control member 30 and the housing 50. The housing nut 85 is then threaded over the body portion 52 of the housing 50 through engagement of the outer threaded surface 60 of the housing 50 with the inner threaded surface 89 of the housing nut 85. A user may grasp the longitudinal ribs 90 of the housing nut 85 to assist in threading the housing nut 85 onto the housing 50.

Although the air control member 30, the housing 50, scent container 65, and housing nut 85 are secured to each other using a corresponding thread engagement, the air control member 30, housing 50, scent container 65, and housing nut 85 may have any suitable fastening or securing arrangement. For example, the scent container 65 may have a friction fit engagement with the air control member 30. Moreover, although the scent container 65 is shown disposed with the air control member 30, the scent container 65 may be positioned differently relative to the air control member 30 such that the scent openings 74 are still in fluid communication with the central passageway 95 or air passing through the air control member 30. For example, the scent container 65 may be positioned on an end of the air control member 30 opposite the closed top 35.

Referring to FIG. 4, the flange 92 of the housing nut 85 and the flange 54 of the housing 50 are configured to clamp a bathtub deck 101 or other portion of material therebetween. In particular, the housing 50, with the air control member 30 and the scent container 65 at least partially positioned within the housing 50, may be inserted into an opening in a bathtub deck 101. The housing nut 85 is then threaded onto the body portion 52 of the housing 50 such that the housing nut 85 engages the bathtub deck 101 to secure the air control and aromatherapy module 25 to the bathtub deck 101. A bead of sealant (not shown), such as a silicon sealant, may also be provided between the housing nut 85 and the bathtub deck 101 as well as between the housing 50 and the bathtub deck 101. With the housing 50 secured to the bathtub deck 101, the air control member 30 may be selectively displaced relative to the housing 50 by rotating the air control member 30 within the housing 50. In particular, the air control member 30 may be displaced such that the portion of the intake opening 38 extending beyond the housing 50 may be adjusted. For example, the intake opening 38 may be completely covered by rotating the air control member 30 such that the closed top 35 of the air control member 30 engages the flange 54 of the housing 50. By rotating the air control member 30 in the opposite direction, the intake opening 38 of the air control member 30 may be extended only partially beyond the housing 50, as shown in FIG. 4, or may extend completely beyond the housing 50.

Figure 13:
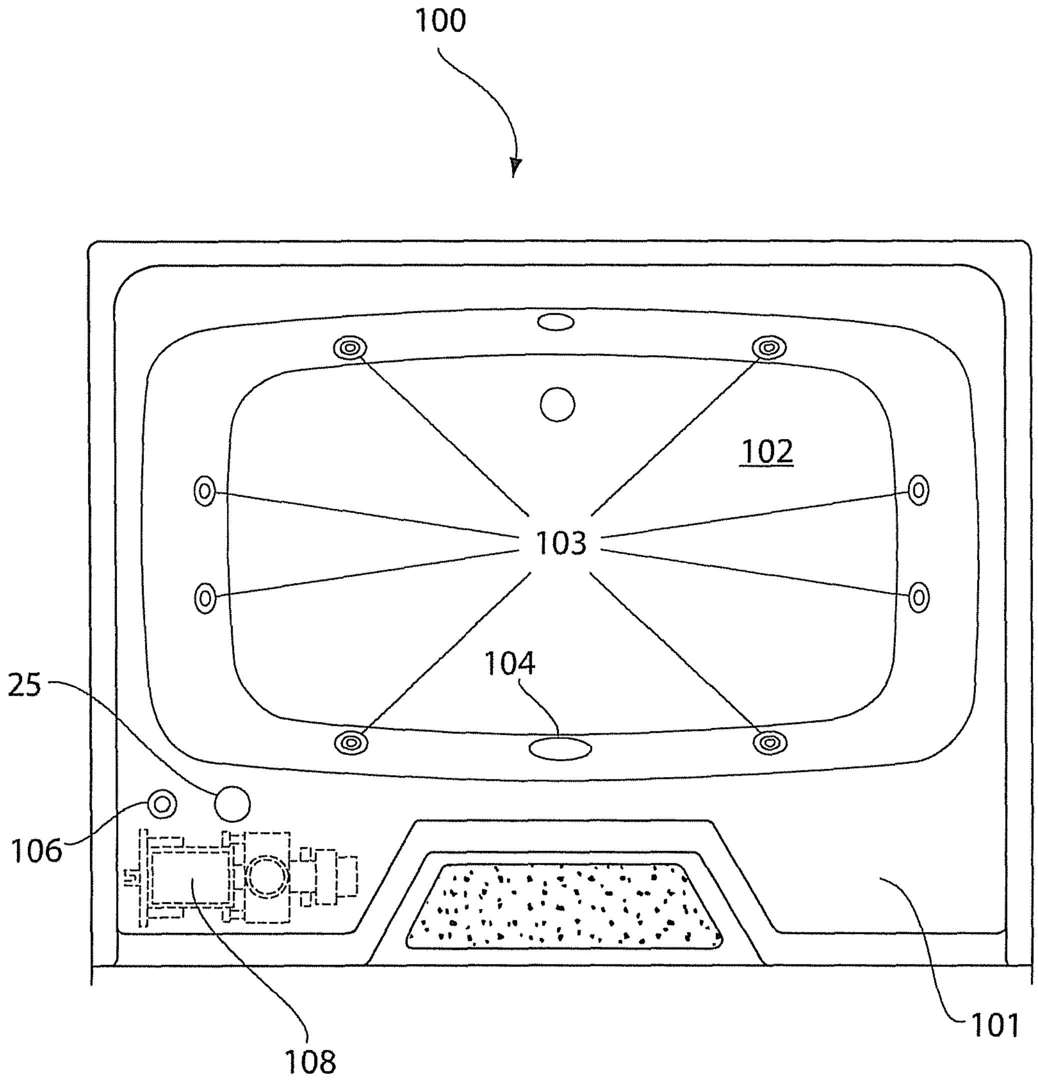
FIG. 13 is a schematic view of a whirlpool bathtub illustrating the positioning of the module shown in FIG. 2 on the bathtub according to one embodiment of the present invention.

Referring to FIG. 13, the positioning of the air control and aromatherapy module 25 on a whirlpool bathtub 100 according to one embodiment is disclosed. The whirlpool bathtub 100 includes a bathing well 102 having a plurality of jets 103 and a water inlet 104. The bathtub 100 further includes an on/off control 106 and a whirlpool pump 108. The air control and aromatherapy module 25 is positioned on the bathtub deck 101 of the whirlpool tub 100 as discussed above. Although the on/off control 106, whirlpool pump 108, and the air and aromatherapy control 25 are positioned generally adjacent to each other, the on/off control 106, pump 108, and air control and aromatherapy module 25 may have any suitable position or configuration within the bathtub 100.

During operation, the on/off control 106 selectively activates the whirlpool pump 108 to circulate water between the water inlet 104 and the jets 103 positioned within the bathing well 102 of the bathtub 100 via a common water line (not shown). The air control and aromatherapy module 25 is connected to the jets 103 via a common air line (not shown). The common air line may be secured to the housing 50 of the air control and aromatherapy module 25. The water line and the air line may be constructed from polyvinyl chloride (PVC), although other suitable materials for the lines may be used. Due to the water passing through the water lines, air is drawn within or directed to the intake opening 38 of the air control member 30 by venturi, principles through the air line and into the stream of water exiting the jets 103. In other words, a negative pressure is created by the water exiting the jets 103 to pull air through the intake opening 38 of the air control member 30, which passes through the central passageway 95, into the air line, and out the jets 103. The scent openings 74 of the scent container 65 are in fluid communication with the central passageway 95 such that the air entering the intake opening 38 passes through an aromatherapy catalyst in the scent container 65 and through the scent openings 74 for delivery to the jets 103. Accordingly, the air entering the intake opening 38 contacts the aromatherapy catalyst and carries the scent into the bathing well 102 when the air is mixed with the water in the jets 103. By selectively displacing the air control member 30 to change the amount that the intake opening 38 extends beyond the housing 50, as discussed above, the quantity of air passing through the intake opening 38 and through the scent container 65 and delivered to the jets 103 can be controlled as desired.

While certain embodiments of the air control and aromatherapy module were described in the foregoing detailed description, those skilled in the art may make modifications and alterations to these embodiments without departing from the scope and spirit of the invention. Accordingly, the foregoing description is intended to be illustrative rather than restrictive.

The invention claimed is:

1. An air control and aromatherapy module for a jetted tub comprising:

an air control member having a body portion defining a central passageway and an intake opening; and a scent container defining a scent opening, the scent container at least partially positioned within the air control member; and a housing having a body portion and defining a central passageway, the air control member and the scent container at least partially disposed within the central passageway of the housing, wherein the scent opening of the scent container is in fluid communication with the central passageway of the air control member, and wherein the intake opening of the air control member is displaceable relative to the housing with at least a portion of the intake opening of the air control member configured to extend beyond the central passageway of the housing to control a quantity of air passing through the intake opening for delivery to jets of the jetted tub.

2. The air control and aromatherapy module of claim 1, wherein the scent container comprises a body portion and an end portion defining a receiving space for an aromatherapy catalyst.

3. The air control and aromatherapy module of claim 2, wherein the scent container is positioned within the body portion of the air control member.

4. The air control and aromatherapy module of claim 2, wherein the end portion of the scent container defines the scent opening.

5. The air control and aromatherapy module of claim 1, wherein the air control member further comprises a closed top positioned on an end of the body portion of the air control member.

6. The air control and aromatherapy module of claim 1, wherein the body portion of the air control member is cylindrical in shape having an inner threaded surface and an outer threaded surface, the body portion of the housing is cylindrical in shape having an inner threaded surface, and the scent container is cylindrical in shape having an outer threaded surface.

7. The air control and aromatherapy module of claim 6, wherein the outer threaded surface of the scent container engages the inner threaded surface of the air control member, and the outer threaded surface of the air control member engages the inner threaded surface of the housing.

8. The air control and aromatherapy module of claim 7, wherein the body portion of the housing further comprises an outer threaded portion.

9. The air control and aromatherapy module of claim 8, further comprising a housing nut engaged with the outer threaded portion of the housing.

10. The air control and aromatherapy module of claim 9, wherein the housing further comprises a flange extending from the body portion of the housing, the flange of the housing and the housing nut being configured to engage a tub deck.

11. A method of providing aromatherapy to a jetted tub comprising:

positioning a scent container within an air control member, the scent container configured to receive an aromatherapy catalyst and defining a scent opening, the air control member defining an intake opening in fluid communication with the scent opening of the scent container; and positioning the air control member and the scent container at least partially within a housing and displacing the air control member relative to the housing to position at least a portion of the intake opening of the air control member beyond the housing to control a quantity of air directed through the intake opening of the air control member for delivery to jets of the jetted tub.

* * * * *

UNITED STATES PATENT AND TRADEMARK OFFICE

CERTIFICATE OF CORRECTION

PATENT NO. : 8,671,472 B2
APPLICATION NO. : 12/469275
DATED : March 18, 2014
INVENTOR(S) : David M. Groner et al.

It is certified that error appears in the above-identified patent and that said Letters Patent is hereby corrected as shown below:

In the Claims:

Column 6, Line 5, Claim 1, after "opening;" delete "and"

Signed and Sealed this
First Day of July, 2014

Michelle K. Lee
*Deputy Director of the United States Patent and Trademark Office*